United States Patent
Xu et al.

(10) Patent No.: US 7,271,298 B2
(45) Date of Patent: Sep. 18, 2007

(54) PROCESS FOR ISOLATION AND PURIFICATION OF XANTHOPHYLL CRYSTALS FROM PLANT OLEORESIN

(75) Inventors: Xinde Xu, Xinchang (CN); Bin Shao, Xinchang (CN); Di Zhou, Xinchang (CN); Shuangming Ye, Xinchang (CN); Yanfeng Wang, Xinchang (CN); Boqiu Chen, Xinchang (CN)

(73) Assignee: Zhe Jiang Medicine Co., Ltd. Xinchang Pharmaceutical Factory, Xinchang (CN)

( * ) Notice: Subject to any disclaimer, the term of this patent is extended or adjusted under 35 U.S.C. 154(b) by 0 days.

(21) Appl. No.: 11/336,869

(22) Filed: Jan. 23, 2006

(65) Prior Publication Data

US 2007/0032683 A1 Feb. 8, 2007

(30) Foreign Application Priority Data

Aug. 3, 2005 (CN) .................. 2005 1 0028396

(51) Int. Cl.
*C07C 35/21* (2006.01)
(52) U.S. Cl. .................................... 568/816
(58) Field of Classification Search ........... 568/834, 568/816
See application file for complete search history.

(56) References Cited

U.S. PATENT DOCUMENTS

| 5,382,714 | A | 1/1995 | Khachik |
| 5,648,564 | A | 7/1997 | Ausich |
| 6,262,284 | B1 | 7/2001 | Khachik |
| 6,329,557 | B1 | 11/2001 | Rodriguez |
| 6,380,442 | B1 | 4/2002 | Madhavi |
| 6,504,067 | B1 * | 1/2003 | Montoya-Olvera et al. .................. 568/816 |
| 6,743,953 | B2 | 6/2004 | Kumar |

OTHER PUBLICATIONS

Bone et al., Invest Ophthamal. Vis. Sci. 34:2033-2040 (1993).
Seddon et al., J. Am. Med. Assoc. 272: 1413-1420 (1994).

* cited by examiner

*Primary Examiner*—Johann Richter
*Assistant Examiner*—Jennifer Cho
(74) *Attorney, Agent, or Firm*—Manni Li; Perkins Coie LLP

(57) ABSTRACT

A process for isolation and purification of xanthophylls crystals from plant oleoresin is disclosed. The organic solvents involved in the process is no other than food grade alcohol. The process includes saponifying the plant oleoresin containing xanthophyll diesters, neutralizing the saponified reaction mixture with an acid and washing water-soluble impurities and other fat-soluble oil with warm water and alcohol, respectively. The process can improve purity and yield of products, by which the content and the recovery of xanthophylls are as high as 90% and 80% respectively. And the process is economical and easy to perform in industrial production.

11 Claims, No Drawings

PROCESS FOR ISOLATION AND PURIFICATION OF XANTHOPHYLL CRYSTALS FROM PLANT OLEORESIN

BACKGROUND OF THE INVENTION

1. Field of the Invention

The present invention relates to a simultaneous process for isolation and purification of lutein and zeaxanthin from crude plant oleoresin, preferably marigold extracts with high yield rate.

2. Description of the Prior Art

Carotenoids are yellow, red and orange pigments which are widely distributed in nature. In different fruits and vegetables, there are specific carotenoids, for example, β-carotene in carrots, lutein in marigold flowers, zeaxanthin in strawberry, capsanthin and capsorubin in the pepper plant, and lycopene in tomatoes, etc. Besides xanthophylls in fruits and vegetables, in egg yolks, some fish crustaceans, birds, algae and bacteria, there are also some other carotenoids.

In recent years, human and animal studies have revealed various beneficial effects of carotenoids. Carotenoids are classified into two sub-classes, namely, more polar compounds called xanthophylls or oxy-carotenoids like lutein, zeaxanthin and astaxanthin and non-polar hydrocarbon carotenes like β-carotene, lycopene, etc. Both the sub-classes have at least nine conjugated double bonds which not only are responsible for the characteristic colors of the carotenoids, but also endow them with the function as antioxidants in disease prevention, which may retard or prevent diseases like cancer, arteriosclerosis, cataracts, macular degeneration and others, because carotenoids are effective quenchers of the highly reactive oxygen free radicals and can also prevent generation of free radicals, thereby limiting free radical oxidative damage.

Among kinds of carotenoids, lutein and zeaxanthin recently are paid considerable attention from scientists and public to with respect to their potential role in prevention of an eye disease, namely, Age-Related Macular Degeneration (ARMD). Lutein and zeaxanthin are the only carotenoids present in the macular region of the human retina and are related to a normal function of the macular region responsible for visual acuity (Bone et al. Invest. Ophthalmal. Vis. Sci. 34: 2033-2040, 1993). High consumption of fruits and vegetables riched specifically in lutein and zeaxanthin is correlated to a 43% lower risk of ARMD (Seddon et al. J. Am. Med. Assoc. 272: 1413-1420, 1994) and metabolic pathways for these compounds in the prevention of ARMD have been proposed, too. Food and Drug Administration also considers lutein and zeaxanthin as GARS. Therefore, these carotenoids may be used, individually or in combination, as nutritional supplements and food colorants as well as in clinical trials where their potential health benefits in the prevention of ARMD and cancer can be investigated.

While a process for chemical syntheses of xanthophylls involves multiple steps, and is extremely time-consuming, a more economical route to get large-scale production of xanthophylls is a process that extracts, isolates and purifies xanthophylls from nature sources.

Although being present in many vegetables and fruits such as spinach, broccoli, kale and corn, marigold flowers are the richest sources of lutein, along with other carotenoids, which generally occur esterified with mono- or di-$C_{12}$-$C_{18}$ long chain fatty acids such as lauric acid, myristic acid, oleic acid, linoleic acid and palmitic acid.

The xanthophyll esters are extracted from the plant, preferably from marigold flowers and other deep-green vegetables with organic solvents, which themselves were readily removable from the extract. The extract from the petals of marigold flowers (marigold oleoresin) is an excellent resource of lutein esters in large quantities and contains no significant levels of other carotenoids. After saponified under alkaline condition, the xanthophylls in the free form are obtained, the resultant alkali salts of fatty acids obtained from the saponification are removed and the xanthophylls are purified further.

Several patents and publications propose processes for isolation of lutein from marigold petals on a commercial scale. In general, the publications focus on the isolation of lutein in a pure crystal form and involve multiple steps.

U.S. Pat. No. 5,382,714 teaches isolation and purification of lutein from saponified marigold oleoresin by washing with water at a low temperature and then crystallizing in solvent mixtures also at a low temperature. The purification steps are very time consuming and halogenated organic solvent was used, which is not suitable for food or pharmaceuticals.

U.S. Pat. No. 5,648,564 disclosed a process for isolation and purification lutein from marigold oleoresin saponified in alkaline propylene glycol solutions, followed by recrystallization. This process has several disadvantages: firstly, due to high viscosity of the propylene glycol, the saponified and handling process requires a high temperature up to 70° C. for over 10 hours, and this would be harmful for the stabilities of xanthophylls. The following isolation process such as centrifugation or filtration are difficult to be handled, too. Secondly, recovery of lutein is as low as around 59 percent, the content of lutein is not high, too.

U.S. Pat. No. 6,262,284 describes the simultaneous extraction and saponification of carotenoids from marigold dry flower petals with THF, which results in the use of large volumes of solvent, and the solvent also is unstable and so produces may degrade because of being peroxided.

U.S. Pat. No. 6,329,557 develops an industrial scale process for obtaining xanthophyll crystals from marigold oleoresin. The disadvantages of the process are that amounts of organic solvent such as hexane and ketone were used, and these organic solvents are not suitable for food additive.

U.S. Pat. No. 6,380,442 reports a process for isolation of mixed carotenoids from plants, the process is not attractive for commercial applications since more than 30 volumes of water is required for per weight of the input material.

U.S. Pat. No. 6,743,953 employs kinds of organic solvents to isolate and purify xanthophylls from marigold oleoresin. In the process, isopropyl alcohol, ethyl acetate, hexane, acetone and methanol were used, therefore, the method is not welcomed in industrial production.

The disadvantages of these processes described above are that: i) Some toxic organic solvents were used, which were difficult or impossible to remove, resulting in xanthophyll crystals being not suitable for human consumption; ii) It is difficult to handle in the process of isolation or purification because of the high viscosity of solvents and several steps are involved to isolate and succeeded purify the crystals, so it is not attractive for industrial production; iii) There are many steps in the operation, which results in a low recovery of xanthophylls which is usually around 50%.

Thus, there remains a need for an industrial process for obtaining lutein and zeaxanthin concentrates with high purity and as little as possible toxic organic solvent and operation steps, and with high yield rate. The process disclosed herein after will provide such a convenient but effective way to provide a comestible xanthophyll.

SUMMARY OF THE INVENTION

The present invention provides a convenient and commercial viable process for preparation of xanthophylls, especially lutein, from plant oleoresin containing xanthophyll-diesters with minimal use level of organic solvents but high recovery.

The levels of xanthophylls in the product, which may be applicable for human use, are around 90%, in which the content of all-trans lutein is at least 90% and the remaining is zeaxanthin, trace amount of cis-lutein and other carotenoids.

The process involves hydrolyzing carotenoid esters in plant oleoresin using ethanol, water and alkali, for 3 to 5 hours at a temperature of about 40 to 85° C., then neutralizing the saponified reaction mixture with acid water. The precipitated crystals is recovered by centrifugation or filtration, followed by purification of the precipitate with water and alcohol mixture washing repeatedly. After recrystallization at an ambient temperature with alcohol, a drying step is taken to obtain a fine crystalline material.

The present invention provides a process for preparation of xanthophylls crystals containing at least 80% total xanthophylls with at least 90% trans-lutein and/or zeaxanthin and trace amount of cis-lutein and other carotenoids from plant oleoresin that contains xanthophyll-diesters, and the process includes the steps of:

a) saponifying homogeneous liquid of the plant oleoresin containing xanthophyll diesters and alcohol by adding an aqueous alkali solution thereto at a temperature in the range of 40 to 85° C. for 3-5 hours;

b) cooling the saponified reaction mixture to an ambient temperature, and the pH is adjusted to 1-7, preferably to 6-7;

c) admixing 2 to 10 volumes of water and 0.5 to 2 volumes of alcohol per weight of the plant oleoresin, increasing the temperature to 40° C. to 85° C., agitating slowly for a period of 0.5 to 2.0 hours, thereby forming crystalline precipitate;

d) recovering xanthophyll crystals from the crystalline precipitate by separating;

e) washing the xanthophyll crystals 2-3 times with water at a temperature of 70-85° C. until supernatant is colorless; and f) leaching the xanthophyll crystals with dry ethanol and drying the xanthophyll crystals in vacuum or freeze drying the xanthophyll crystals to have less than 5% moisture content.

Advantageously, the plant oleoresin containing xanthophylls-diesters is extracted from at least one of marigold flower, wolfberry, spinach, kale and broccoli.

Advantageously, the step a) further comprising adding 0.1 to 2.0 volumes of the alcohol per weight of the plant oleoresin to the plant oleoresin to obtain the free flowing homogeneous liquid under agitation at a temperature of 60 to 65° C.

Advantageously, the alkali solution is a potassium hydroxide solution or a sodium hydroxide solution, and a ratio of weight of alkali in the alkalin solution to that of the plant oleoresin is from 1:4 to 1:8.

Advantageously, the step b) further comprising adding an acid to adjust the pH to 1-7, the acid is at least one of organic acid and inorganic acid.

Advantageously, the step b) further comprising adding an acid to adjust the pH to 1-7, the acid is at least one of phosphoric acid, sulfuric acid, hydrochloric acid and acetic acid.

Advantageously, the step c) further comprising the water is deionized water.

Advantageously, the step c) further comprising separating the crystalline precipitate by centrifugation, filterpressing or filtration.

Advantageously, the alcohol is at least one of means methanol, ethanol, isopropanol and propanol.

The advantages of this invention is as follows: first, the organic solvents involved in the process is no other than food grade alcohol, the product is safely used as nutritional supplements or food coloring additives; secondly, because of low viscosity of water and alcohol, it is relative easy to operate during the process of separation; thirdly, after neutralizing the saponified mixture, water-soluble impurities and other fat-soluble oil can be washed with warm water and alcohol, respectively, which is beneficial to purifying the last product; fourthly, the content and the recovery of xanthophylls are as high as 90% and 80% respectively, they are much higher than those revealed in former technologies. So the process is economical and easy to perform on a large commercial scale. These and other advantages will become readily apparent to those skilled in the art based on the disclosure set forth herein.

DETAILED DESCRIPTION OF THE INVENTION

The present invention disclose a process for isolation and purification of lutein and zeaxanthin from nature sources, such as marigold flowers extracts, kale, spinach, broccoli and corn. Among these sources, marigold flowers extracts are a preferential source since they have relatively high levels of xanthophylls.

In the invention, commercially available food grade marigold oleoresin produced by hexane extraction can be used as starting material for the isolation of an all-trans lutein enriched product. Based on cultivar, meal quality and extraction processes, the oleoresin contents about 5 to 30% lutein esters and other carotenoids such as all-trans zeaxanthin, $\alpha$- and $\beta$-cryptoxanthin and $\beta$-carotene.

In the present invention, food grade marigold oleoresin is dissolved in food grade alcohol to form a free flowing solution at a temperature within the range from about 40 to 85° C. In a typical process, one weight part of the oleoresin is dissolved in 0.1-2.0 volume parts of the solvent. The xanthophyll esters, as well as other impurities such as wax, resin, other carotenoids and pigments, are dispersed/dissolved in the solvent to form a homogeneous liquid under agitation.

A 45 percent potassium hydroxide solution, for example, is added slowly to the dissolved/dispersed oleoresin over a period of time to form a saponified reaction mixture. The amount of the alkali required is approximately 1.0 to 3.0 times as heavy as the weight of the oleoresin containing xanthophyll-diesters. The mixture is maintained at the same temperature as 40 to 85° C. under agitation till the saponification reaction is complete, it usually needs 3-5 hours. Whether the saponification is complete or not can be readily determined by a thin layer of chromatography (TLC). The alkali used in this step could be sodium hydroxide or potassium hydroxide or some other alkali.

Free lutein, zeaxanthin and other xanthophylls are obtained during the saponification reaction, as well as sodium salts or potassium salts of fatty acids like myristic acid, palmitic acid and stearic acid.

The pH of the mixture is then adjusted to about 1.0 to 7.0, and preferably, about 5.0 to 6.5, with aqueous solutions of an acid selected from any organic acid such as citric acid and succinic acid or any inorganic acid such as hydrochloric acid, sulfuric acid, phosphoric acid, etc. The concentration of the acid solution can be fixed from 10% to 40% (w/w). The neutralizing reaction occurs at a temperature ranged from 40° C. to 85° C., over a period of 10 to 30 minutes under gentle agitation.

The neutralized mixture is allowed to be cooled to about 60° C. Then a sufficient quantity of deionized water and alcohol mixture, preferably ethanol, is added to reduce the solute concentration to about 10-50% (v/v) by slow mixing. The volume of the deionized water is 1-4 times as large as the weight of oleoresin and the volume of the alcohol is 1-2 times as large as the weight of oleoresin. The ratio of the volume of the deionized water to the weight of the plant oleoresin is 2:1-10:1. The ratio of the volume of the alcohol to the weight of the plant oleoresion is 0.5:1-2:1. The temperature of the mixture rises to about 50-70° C. and maintains at this temperature under gentle agitation. Then the solution is allowed to keep for about 1-2 hours till the lutein and other carotenoids separate as a fine crystalline precipitate.

The xanthophylls are recovered from the crystalline precipitate by traditional separation ways such as centrifugation, filtration, filterpressing, etc. Prior to the separation, the mixture could be diluted with a certain amount of warm water and alcohol to reduce the total carotenoid concentration. After separation, the impurities, such as fatty acids, salts, soaps, water soluble chlorophylls, flavonoids and so on, are removed in the supernatant, and the lutein and the zeaxanthin are rich in the collected solid.

Additional recovery efforts may include, for example, that the precipitate can be washed with additional water and ethanol mixture at a temperature ranged from 60° C. to 80° C. til the supernatant becomes almost colorless. Usually 2-3 times washes are sufficient to remove most of contaminants. At last, the crystal could be washed with dry ethanol, which would make it more easier to be dried. The washed precipitate can be dried in a suitable method such as vacuum drying, rotary vacuum drying at 40° C. and freeze drying, till the moisture level is reduced to less than about 5%.

It is noted that purity and overall yield of the final product are influenced not only by the solvent percentage used in the saponified mixture and the volume of the added alcohol in the diluted blend materials, but also by the time of precipitation. Less concentration of xanthophyll esters in the solvent because of more quantities of the solvent would result in less recovery and lower content of caretenoids in the crystals, while less solvent would make the viscosity become higher and be adverse to the saponified reaction and the later separation process. During the diluting process before separation, overabundance alcohol would reduce the yield rate of xanthophylls while too little alcohol may increase difficulty of operation, too. The time for precipitation should not be too short, otherwise the recovery of total xanthophylls could not reach a high level.

Based on spectrophotometry and HPLC, the resulting crystal obtained by this present process contains about 85 to 95 percent carotenoids, which contain 90 to 95 percent all-trans lutein, 0.1 to 1.0 percent of geometrical isomers thereof, 2.0 to 7.0 percent all-trans zeaxanthin and less than 1.0 percent trace amount of other carotenoids.

It is not concerned at all that the low levels of these carotenoids are present, since these carotenoids are dietary origins and are found routinely to have much higher concentrations relative to that of lutein in human serum or plasma.

No organic solvents other than food grade alcohol is used in this process, and therefore, the substantially pure crystal obtained through this process does not contain residues of toxic organic solvents or other toxic-compounds, and is suitable for human consumption.

The operation of HPLC is listed as follows:
Chromatographic Column: 250 mm*4.6 mm beta-cyclodetrin;
Column Temperature: ambient temperature;
Mobile Phase: Hexane/acetone(85/15) filtered through a 0.45 µm membrane;
Flow rate: 1.5 ml/min;
Detector wavelength: 445 nm;
Injection volume: 10 µl;
Preparation of Specimens: weigh out about 27-30 mg of the product and transfer it to a 100 ml volumetric flask; add 20 ml of dry ethanol and make it dissolve with ultrasonic; add dry ethanol to the 100 ml mark. Evaporate the solution to dryness under vacuum at 45° C. with nitrogen gas; dissolve residue with 1 ml mobile phase and inject 10 µl of this solution into HPLC and detect it at wavelength of 446 nm.

It is possible that changes could be effects in the embodiment described above without deviating from the broad spectrum of the concept of the invention. Therefore, it is to be noted that this invention is not limited to the particular embodiments disclosed herein but it is intended to cover all modifications falling within the scope of the appended claims.

The details of the process of the invention are given in the embodiments provided below which are provided only by way of illustration and therefore should not limited to the scope of the prevent invention.

THE FIRST EMBODIMENT 1000 g of marigold oleoresin containing 16.3% total xanthophylls is mixed with 1000 ml ethanol with stirring and heated to a temperature of 75° C. till a free flowing solution has been obtained. 375 ml 45 percent sodium hydroxide solution is added slowly and evenly over a period of 60 minutes with stirring. The saponification process maintains for 4 hours at 75° C. with gentle agitation.

The reaction mixture is allowed to be cooled to 60° C. The pH is adjusted to 6-7 with a 25% aqueous solution of acetic acid. After gentle mixing for 10 minutes, the reaction mixture is added 2000 ml deionized water and 400 ml ethanol to, and during the diluting process, the temperature of the mixture keeps about 65° C. After agitated for 30 minutes until homogenous, the blend is fed into a centrifuge to separate the crystals. This operation is easy to be performed and only takes about 10 minutes to complete. The collected fine crystalline precipitate is washed 2-3 times with deionized water at 75° C. till the supernatant becomes almost colorless. After being leached with dry ethanol, the crystals are dried under vacuum at 40° C. to less than 5% moisture content.

The yield of the final product is 150.4 g, which contains 95.6% total carotenoids (as determined by spectrophotometry) of which 91.4% is all-trans lutein, 4.8% is all-trans zeaxanthin (as determined by HPLC), and the rest contains trace amount of other carotenoids. The recovery of xanthophylls is 85% of the total xanthophylls present in the oleoresin.

The product contains no toxic organic solvents, and is suitable for human consumption and can be used as a nutritional supplement and as an additive in food. The applicable forms of the crystal can be oil suspension (blending with vegetable oil), beadlet (spray-cooling through microencapsulation technology) and microencapsulation powders.

THE SECOND EMBODIMENT

The studies in the second embodiment are performed with the same materials and in the same way as used in the first embodiment except that the reaction mixture need not be neutralized with acid. Directly add 65° C. 2000 ml deionized water and 400 ml ethanol into the reaction mixture, agitate for 30 minutes, and use the same centrifuge as present in the first embodiment to separate the crystals. The saponified mixture was more difficult to be centrifuged and over 30 minutes are required to separate the supernatant completely.

The recovery of xanthophylls was 82% of the total xanthophylls present in the starting materials.

THE THIRD EMBODIMENT 1000 g of marigold oleoresin containing 14.5% total xanthophylls is mixed with 2000 ml ethanol. A free flowing solution is obtained when the temperature is increased to 60° C. under agitation. Then 500 ml 45 percent potassium hydroxide solution is dropped and added. The saponification reaction keeps 4 hours at 75° C. with slowly mixing.

The reaction mixture is neutralized with a 25% aqueous solution of hydrochloric acid after the temperature drops to 60° C., till the pH is adjusted to 6.0-6.5. After agitated for 30 minutes, the reaction mixture is added 2000 ml deionized water and 800 ml ethanol to, and the blend mixture is heated to 65° C. and maintained for a period of 0.5 hours under gentle agitation till the xanthophyll crystal appears. After a separating process with centrifugation as operated in example 1 for a period of 15 minutes, the relative drying precipitate is collected.

The gained fine crystalline is washed 2-3 times with 75° C. deionized water until the supernatant becomes almost colorless. After being leached with dry ethanol, the precipitates are dried under vacuum at 40° C. to have less than 5% moisture content.

The yield of the final product is 104.5 g, which contains 75.4% total carotenoids (as determined by spectrophotometry) of which 90.8% is all-trans lutein, 6.2% is all-trans zeaxanthin (as determined by HPLC), and the rest is trace amount of other carotenoids. The recovery of xanthophylls is 54.3%.

Through the latter two examples, the efficacy of the present invention is demonstrated.

What is claimed is:

1. A process for preparing xanthophylls comprising the steps of:
    a). saponifying a homogeneous liquid mixture of a xanthophyll diester-containing plant oleoresin and an alcohol by adding an aqueous alkali solution to the mixture and mixing at a temperature in the range of 40 to 85° C. for 3-5 hours, wherein a ratio of the weight of the alkali in the aqueous alkali solution to that of the plant oleoresin is about 1:8 to 3:1;
    b). cooling the saponified reaction mixture to an ambient temperature, and adjusting its pH to 1-7;
    c). admixing 2 to 10 volumes of water and 0.5 to 2 volumes of the alcohol per weight of the plant oleoresin with the cooled mixture, increasing the temperature to 40° C. to 85° C., and agitating slowly for a period of 0.5 to 2.0 hours to form crystalline precipitate;
    d). separating and recovering xanthophyll crystals from the crystalline precipitate;
    e). washing the xanthophyll crystals 2-3 times with water at a temperature of 70-85° C. until supernatant is colorless; and
    f). leaching the xanthophyll crystals with dry ethanol and drying the xanthophyll crystals to less than 5% moisture content.

2. The process as claimed in claim 1, wherein the xanthophyll diester-containing plant oleoresin is extracted from at least one of food grade marigold flower, wolfberry, spinach, kale, or broccoli.

3. The process as claimed in claim 1, further comprising adding 0.1 to 2.0 volumes of the alcohol per weight of the plant oleoresin to the plant oleoresin and agitating at a temperature of 60 to 65° C. to obtain a free flowing homogenous liquid mixture prior to saponification in step a).

4. The process as claimed in claim 1, wherein the alkali solution is a potassium hydroxide solution or a sodium hydroxide solution, and a ratio of weight of alkali in the alkaline solution to that of the plant oleoresin is from 1:4 to 1:8.

5. The process as claimed in claim 1, further comprising adding an acid to adjust the pH to 1-7 in step b), wherein the acid is an organic acid, an inorganic acid, or both.

6. The process as claimed in claim 5, wherein the acid is at least one selected from the group consisting of phosphoric acid, sulfuric acid, hydrochloric acid, and acetic acid.

7. The process as claimed in claim 1, wherein the water is deionized water in step c).

8. The process as claimed in claim 1, wherein the xanthophyll crystals are separated from the crystalline precipitate by centrifugation, filterpressing, or filtration.

9. The process as claimed in claim 1, wherein the alcohol is at least one selected from the group consisting of methanol, ethanol, isopropanol, and propanol.

10. The process as claimed in claim 1, wherein the pH is adjusted to 6-7 in step b).

11. The process as claimed in claim 1, wherein the alcohol is food grade ethanol.

* * * * *